(12) United States Patent
Borch et al.

(10) Patent No.: US 6,624,129 B1
(45) Date of Patent: Sep. 23, 2003

(54) LIPASE VARIANT

(75) Inventors: Kim Borch, Copenhagen (DK); Jesper Vind, Lyngby (DK); Allan Svendsen, Horsholm (DK); Dorte Aaby Halkier, Birkerod (DK); Shamkant Anant Patkar, Lyngby (DK); Kirsten Bojsen, Hellerup (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/630,250

(22) Filed: Aug. 1, 2000

Related U.S. Application Data

(63) Continuation of application No. PCT/DK99/00068, filed on Feb. 17, 1999.
(60) Provisional application No. 60/076,365, filed on Feb. 27, 1998.

(30) Foreign Application Priority Data

Feb. 17, 1998 (DK) ........................................ 1998 00217

(51) Int. Cl.[7] ............... C12N 9/16; C12N 9/20; C12N 1/20; C07H 21/04

(52) U.S. Cl. ..................... 510/226; 435/196; 435/198; 435/252.3; 435/320.1; 435/69.1; 510/305; 510/392; 530/350; 536/23.2; 536/23.7

(58) Field of Search ................... 510/226, 305, 510/392; 435/196, 198, 252.3, 320.1, 69.1; 530/350; 536/23.2, 23.7

(56) References Cited

FOREIGN PATENT DOCUMENTS

| | | |
|---|---|---|
| EP | 0 258 068 A2 | 3/1988 |
| EP | 0 305 216 A1 | 3/1989 |
| WO | WO 92/05249 | 4/1992 |
| WO | WO 94/25577 | 11/1994 |
| WO | WO 95/22615 | 8/1995 |
| WO | WO 96/00292 | 1/1996 |
| WO | WO 97/04079 | 2/1997 |
| WO | WO 97/07202 | 2/1997 |

*Primary Examiner*—Tekchand Saidha
(74) *Attorney, Agent, or Firm*—Jason I. Garbell; Elias J. Lambrias (57) ABSTRACT

The present invention relates to lipase variants having at least 90% identity to the wild-type lipase derived from *Humicola lanuginosa* strain DSM 4109 and having a certain distribution of electrically charged amino acids. The present invention also relates to detergents comprising such lipases.

24 Claims, 4 Drawing Sheets

LIPASE VARIANT

CROSS-REFERENCE TO RELATED APPLICATIONS

This application is a continuation of PCT/DK99/00068 filed on Feb. 17, 1999 and claims priority under 35 U.S.C. 119 of Danish application no. PA 1998 00217 filed on Feb. 17, 1998, and U.S. provisional application No. 60/076,365 filed on Feb. 27, 1998, the contents of which are fully incorporated herein by reference.

FIELD OF THE INVENTION

The present invention relates to lipase variants suited for use in detergent compositions, particularly detergents with a high content of anionic surfactant. More particularly, the invention relates to variants of the wild-type lipase from *Humicola lanuginosa* strain DSM 4109.

BACKGROUND OF THE INVENTION

For a number of years, lipases have been used as detergent enzymes to remove lipid or fatty stains from clothes and other textiles, particularly a lipase derived from *Humicola lanuginosa* (EP 258 068 and EP 305 216) sold under the tradename Lipolase® (product of Novo Nordisk A/S).

WO 92/05249, WO 94/25577, WO 95/22615, WO 97/04079 and WO 97/07202 disclose variants of the *H. lanuginosa* lipase having improved properties for detergent purposes. Thus, WO 97/04079 discloses variants having a peptide addition (extension) at the N-terminal. WO 97/07202 discloses lipase variants with "first wash performance" which are capable of removing substantial amounts of lard from a lard stained swatch in a one-cycle wash.

There is an ever existing need for providing novel lipases with improved properties, in particular improved washing properties in commercial detergents, including detergents with a high content of anionic surfactants. The present invention relates to such novel lipases.

SUMMARY OF THE INVENTION

The inventors have found that variants of Lipolase (wild-type *Humicola lanuginosa* lipase) with a certain distribution of electrically charged amino acids have a particularly good first-wash performance in a detergent solution with a high ratio of anionic to non-ionic surfactant.

The inventors found that the effect is achieved by attaching a positively charged peptide extension at the N-terminal and by imposing certain restrictions on the charge distribution in the region corresponding to amino acid positions 90–101 and at position 210. The inventors further devised a method of developing variants with such performance from Lipolase by attaching a peptide extension at the N-terminal and substituting amino acids in the region 90–101 or in the immediate surroundings in the three-dimensional structure. The lipases may further provide additional benefits, such as whiteness maintenance and dingy cleanup.

Accordingly, the invention provides a lipase which is a polypeptide having an amino acid sequence which:

a) has at least 90% identity with the wild-type lipase derived from *Humicola lanuginosa* strain DSM 4109;

b) compared to said wild-type lipase, comprises a positively charged peptide extension attached to the N-terminal;

c) comprises a negative amino acid in position E210 of said wild-type lipase.

Further, the amino acid sequence may:

d) comprise a negatively charged amino acid in the region corresponding to positions 90–101 of said wild-type lipase; and e) comprise a neutral or negative amino acid at a position corresponding to N94 of said wild-type lipase and/or has a negative or neutral net electric charge in the region corresponding to positions 90–101 of said wild-type lipase.

Alternatively, the amino acid sequence may:

d) comprise amino acids with negative or unchanged electric charge in at least two of positions N94, D96 and E99 of said wild-type lipase.

The invention also provides a detergent composition comprising the lipase, a DNA sequence encoding the lipase, an expression vector harboring the DNA sequence, a transformed host cell containing said DNA sequence or said expression vector, and a method of producing the lipase by culturing the transformed host cell.

Further, the invention provides a method of producing a variant lipase, which method comprises:

a) selecting a parent lipolytic enzyme having an amino acid sequence which has at least 90% identity with the wild-type lipase derived from Humicola lanuginosa strain DSM 4109;

b) modifying the sequence of a nucleic acid encoding the parent lipase to produce a nucleic acid encoding a lipase which comprises a peptide extension at the N-terminal and an amino acid substitution at as location:

i) in the region corresponding to positions 90–101 of said wild-type lipase, or ii) at the surface of the three-dimensional structure within 6 Å of any of the positions 90–101, c) expressing the modified nucleic acid in a host cell to produce the variant lipase, d) testing the first-wash effect of the variant lipase in a detergent solution comprising anionic surfactant in an amount of more than 70% by weight of the total surfactant, e) optionally repeating steps b–d, and f) selecting a variant having improved first-wash effect.

DETAILED DESCRIPTION OF THE INVENTION

*Humicola lanuginosa* Lipase

The reference lipase used in this invention is the wild-type lipase derived from *Humicola lanuginosa* strain DSM 4109. It is described in EP 258 068 and EP 305 216 and has the amino acid sequence shown in positions 1–269 of SEQ ID NO: 2 of U.S. Pat. No. 5,869,438. In this specification, the reference lipase is also referred to as Lipolase.

Peptide Extension at N-terminal

Compared to Lipolase, the lipase of the invention comprises a positively charged peptide extension attached to the N-terminal. The peptide extension preferably consists of 1–15 (particularly 4–10) amino acid residues, and preferably comprises 1, 2 or 3 positively charged amino acids, most preferably 1, 2 or 3 R.

Optionally, the electric charge at the N-terminal may be further increased by substituting E1 with a neutral or positive amino acid, e.g. E1P.

Some preferred peptide extensions are SPIRR (SEQ ID NO: 9), RP(-E), SPIRPRP(-E) (SEQ ID NO: 10), SPPRRP (-E) (SEQ ID NO: 11) and SPIRPRP(-E) (SEQ ID NO: 10). The peptide extension may comprise C (cysteine) attached by a disulfide bridge to a second C in the polypeptide (either C present in Lipolase or introduced by a substitution), e.g. SPPCGRRP(-E) (SEQ ID NO: 12), SPCRPR (SEQ ID NO: 13), SPCRPRP(-E) (SEQ ID NO: 14), SPPCGRRPRRP(-E) (SEQ ID NO: 15), SPPNGSCGRRP(-E) (SEQ ID NO: 16), SPPCRRRP(-E) (SEQ ID NO: 17) or SCIRR (SEQ ID NO: 18) attached to E239C. Such variants may have improved stability.

Further, any peptide extension described in WO 97/04079 and WO 97/07202 may be used.

Amino acids at positions 90–101 and E210

The inventors have found that for good first-wash performance in anionic detergent, amino acid E210 must be negative. Thus, E210 may be unchanged or it may have the substitution E210D/C/Y, particularly E210D.

The lipase may comprise a negatively charged amino acid at any of positions 90–101 (particularly 94–101), e.g. at position D96 and/or E99.

Further, the lipase may comprise a neutral or negative amino acid at position N94, i.e. N94(neutral or negative), e.g. N94N/D/E.

Also, the lipase may have a negative or neutral net electric charge in the region 90–101 (particularly 94–101), i.e. the number of negative amino acids is equal to or greater than the number of positive amino acids. Thus, the region may be unchanged from Lipolase, having two negative amino acids (D96 and E99) and one positive (K98), and having a neutral amino acid at position 94 (N94), or the region may be modified by one or more substitutions.

Alternatively, two of the three amino acids N94, N96 and E99 may have a negative or unchanged electric charge. Thus, all three amino acids may be unchanged or may be changed by a conservative or negative substitution, i.e. N94(neutral or negative), D(negative) and E99(negative). Examples are N94D/E and D96E. Also, one of the three may be substituted so as to increase the electric charge, i.e. N94(positive), D96(neutral or positive) or E99 (neutral or positive). Examples are N94K/R, D96I/L/N/S/W or E99N/Q/K/R/H.

The substitution of a neutral with a negative amino acid (N94D/E), may improve the performance in an anionic detergent. The substitution of a neutral amino acid with a positive amino acid (N94K/R) may provide a variant lipase with good performance both in an anionic detergent and in an anionic/non-ionic detergent (a detergent with e.g. 40–70% anionic out of total surfactant).

Amino acids at other positions

The inventors have found that a substitution of R209 with a neutral or negative amino acid (e.g. R209P/S) may improve the performance in anionic detergent, and that a substitution Q249R/K/H may improve the performance both in anionic and in anionic/non-ionic detergent.

G91 may be unchanged or substituted with another neutral amino acid, e.g. G91G/A/S/T. K 98 may be unchanged, or it may be substituted with a neutral or negative amino acid. N11, D137, E239 may optionally be substituted, e.g. N11E/G/K/Q/R/T, D137C/E/G/N/V/Y, E239D/G/V.

A combination of substitutions E99N+N101S may be used to introduce a glycosylation site.

Combinations of Substitutions

A lipase variant with good performance in anionic detergents may be obtained by combining a peptide extension as described above with one of the following sets of substitutions:

A. G91G/A/S/T+N94(neutral or negative)+D96D/E/C/Y+E99E/D/C/Y

B. G91G/A/S/T+N94(neutral or negative)+D96D/E/C/Y+E99N+N101S

C. G91G/A/S/T+N94R/K/H+D96D/E/C/Y+E99E/D/C/Y

D. G91G/A/S/T+N94(neutral or negative)+D96(neutral or positive)+99E/D/C/Y

E. G91G/A/S/T+N94(neutral or negative)+D96D/E/C/Y+E99(neutral or positive)

F. any of A–E combined with Q249R.

G. any of A–F combined with R209(neutral or negative)

H. any of A–G combined with K98(neutral or negative)

I. Any of the above combinations further combined with any of the substitutions mentioned previously.

A lipase variant with good performance in both anionic and anionic/non-ionic detergents may be obtained by combining a peptide extension as described above with one of the following sets of substitutions:

G91A+E99R/K/H+Q249R/K/H

G91A+N94R/K/H+Q249R/K/H

G91A+D96(neutral or positive)+Q249R/K/H

Nomenclature for Amino Acid Modifications

The nomenclature used herein for defining mutations is essentially as described in WO 92/05249. Thus, E99N indicates a substitution of E in position 99 with N. D96I/L/N/S/W indicates substitution of D in position 96 with I, L, N, S or W. G91G/A/S/T indicates that G91 may be unchanged (G) or substituted with A, S or T. D96X indicates a substitution of D96 with any other amino acid. N94(neutral or negative) indicates a substitution of N94 with any negative or positive amino acid.

SPCRPR (SEQ ID NO: 13) indicates attachment of the peptide extension SPCRPR (SEQ ID NO: 13) at the N-terminal (i.e. E1). E1 SPPCGRRP (SEQ ID NO: 12) or SPPCGRRP(SEQ ID NO: 12) (-E) indicates the substitution E1P and attachment of the peptide extension SPPCGRRP (SEQ ID NO: 12) to the substituted N-terminal.

Amino Acid Grouping

In this specification, amino acids are classified as negatively charged, positively charged or electrically neutral according to their electric charge at pH 10, which is typical of the detergent of the invention. Thus, negative amino acids are E, D, C and Y, particularly E and D. Positive amino acids are R, K and H, particularly R and K. Neutral amino acids are G, A, V, L, l, P, F, W, S, T, M, N, Q. A substitution with another amino acid in the same group (negative, positive or neutral) is termed a conservative substitution.

The neutral amino acids may be divided into hydrophobic (G, A, V, L, I, P, F, W) and hydrophilic (S, T, M, N, Q).

Amino Acid Identity

The lipase variant of the of the invention has an amino acid identity of at least 90% (preferably more than 95% or more than 98%) with Lipolase. For purposes of the present invention, the peptide extension at the N-terminal is disregarded in the calculation of amino acid identity.

The degree of identity may be suitably determined by means of computer programs known in the art, such as GAP provided in the GCG program package (Program Manual for the Wisconsin Package, Version 8, August 1994, Genetics Computer Group, 575 Science Drive, Madison, Wis., U.S.

53711) (Needleman, S. B. and Wunsch, C. D., (1970), Journal of Molecular Biology, 48, 443–45), using GAP with the following settings for polypeptide sequence comparison: GAP creation penalty of 3.0 and GAP extension penalty of 0.1.

The lipase variant of the invention preferably comprises a peptide addition and 0–10 (particularly 2–6) amino acid substitutions.

Method of Producing Variant Lipase

As stated above, the invention provides a method of producing a variant lipase from parent lipase. The parent lipase may be Lipolase or a variant thereof, e.g. having substitutions such as:

E99N+N,101S+E239C+Q249R+SPPCGRRP(-E) (SEQ ID NO: 12),

E99K+E239C+Q249R+SPPCGRRP(-E) (SEQ ID NO: 12)

E99K+E239C+Q249R+SPPCGRRP(-E) (SEQ ID NO: 12)

The variant lipase comprises a peptide extension and an amino acid substitution. The peptide extension at the N-terminal (optionally combined with a substitution of E1) is described above.

The amino acid to be substituted may be in the region corresponding to positions 90–101 (preferably 94–101). Alternatively, the amino acid to be substituted may be at the surface of the three-dimensional structure of the lipase within 6 Å of any of the positions 90–101, e.g. an amino acid at position 83, 85–115, 118, 147, 154, 174, 176–178, 181, 202–203, 206–208, 211–213, 255 or 258.

Preferred amino acids are those in region 90–101 or immediately adjacent to these, i.e. in direct contact with an amino acid in the region. Such amino acids are D102, S105, S115, D111, G112, G106, C107, R108, N178, G212, F211, P208, P207, L206, I202. Amino acids of particular interest are R108, D111, S115, N178, F211, G212, G112, especially R108 and D111.

It is of special interest to substitute with an amino acids with a different electric charge, e.g. to substitute a neutral or positive amino acid with E, D, Y or C; a neutral or negative amino acid with R, K or H; or to substitute a positive or negative amino acid with L, I, V, A, N or Q.

The modification of the DNA sequence may be done by methods known in the art, e.g. site-directed mutagenesis or localized random mutagenesis.

DNA Sequence

The DNA sequence encoding the lipase variant may suitably be prepared by introducing the relevant mutations in a cDNA or genomic DNA sequence encoding the parent lipase. The mutations may be introduced in accordance with well-known techniques such as those disclosed by Sambrook et al. The DNA construct may further comprise control sequences necessary for achieving expression of the modified DNA sequence. The control sequence may be an appropriate promoter sequence, a nucleic acid sequence which is recognized by a host cell for expression of the nucleic acid sequence. The promoter sequence contains transcription and translation control sequences which mediate the expression of the first wash lipolytic enzyme. The promoter may be any nucleic acid sequence which shows transcriptional activity in the host cell of choice and may be obtained from genes encoding extracellular or intracellular polypeptides either homologous or heterologous to the host cell.

The control sequence may also be a suitable transcription terminator sequence, a sequence recognized by a host cell to terminate transcription. The terminator sequence is operably linked to the 3' terminus of the nucleic acid sequence encoding the lipase variant. The terminator sequence may be native to the nucleic acid sequence encoding the lipase variant or may be obtained from foreign sources.

The control sequence may also be a suitable leader sequence, a polyadenylation sequence, a signal peptide encoding sequence, or any other transcriptional or translational regulatory sequence. In addition, the DNA construct may comprise a DNA sequence encoding a factor necessary for producing, the lipase variant in active form, a so-called lipase modulator or chaperone, cf. WO 91/00908, WO 93/13200 and EP 331 376.

Expression Vector

The expression vector of the invention may comprise control sequences as described above necessary for the proper expression of the DNA sequence encoding the lipase variant of the invention. The choice of expression vector will depend, e.g., on the host cell intended for use in the production of the lipase. Suitable expression vectors are disclosed, e.g., in WO 91/00908, WO 93/13200, EP 331 376 and WO 95/14783.

Host Cell

The host cell may be a unicellular microorganism or a non-unicellular micro-organism. The host cell may be a eukaryote, and is preferably a fungal, i.e. a yeast cell or a filamentous fungal cell.

The fungal host cell is preferably a filamentous fungal cell, such as a cell of Acremonium, Aspergillus, Fusarium, Humicola, Myceliophthora, Mucor, Neurospora, Penicillium, Thielavia, Tolypocladium, and Trichoderma, particularly Aspergillus or Fusarium, e.g. *A. oryzae, A. niger, A. foetidus, A. japonicus, F. oxysporum* or *F. graminearum.*

Fungal cells may be transformed by a process involving protoplast formation, transformation of the protoplasts, and regeneration of the cell wall in a manner known per se. Such methods are well known in the art. The host cell is preferably deficient in one or more proteolytic enzymes or other enzyme processing means. Protease deficient host cells are well-known in the art.

The host cell is preferably transformed with a vector comprising a nucleic acid sequence of the invention followed by integration of the vector into the host chromosome. The transformation serves to introduce the vector into the host cell so that the vector is maintained as a chromosomal integrant or as a self-replicating extra-chromosomal vector. Integration may be an advantage as the nucleic acid sequence may be stably maintained in the cell. Integration of the vector into the host chromosome may occur by homologous or non-homologous recombination.

Production of Lipase

The variant lipase of the invention as well as the DNA sequence of the invention, the expression vector of the invention, the transformed host cell of the invention may be prepared by methods well known in the art, e.g. as described in WO 97/04079, and WO 97/07202 or in the examples of this specification.

The host cells may be cultivated in a nutrient medium suitable for production of the lipase variant using methods known in the art. For example, the cell may be cultivated by shake flask cultivation, small-scale or large-scale fermentation (including continuous, batch, fed-batch, or solid state fermentation) in laboratory or industrial fermentors performed in a suitable medium and under conditions allowing lipase variant to be expressed and/or isolated. The cultivation takes place in a suitable nutrient medium comprising carbon and nitrogen sources and inorganic salts, using procedures known in the art (see, e.g., references for bacteria and yeast; Bennett, J. W. and LaSure, L., editors, More Gene Manipulations in Fungi, Academic Press, California, 1991). Suitable media are available from commercial suppliers or may be prepared according to published compositions (e.g., in catalogues of the American Type Culture Collection). If the lipase variant is secreted into the nutrient medium, the variant can be recovered directly from the medium. If the variant is not secreted, it is recovered from cell lysates.

The resulting lipase variant may be recovered by methods known in the art. For example, the variant may be recovered from the nutrient medium by conventional procedures including, but not limited to, centrifugation, filtration, extraction, spray-drying, evaporation, or precipitation. The recovered variant may then be further purified by a variety of chromatographic procedures, e.g., ion exchange chromatography, gel filtration chromatography, affinity chromatography, or the like.

The lipase variant of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., Protein Purification, J. C. Janson and Lars Ryden, editors, VCH Publishers, New York, 1989).

Detergent Additive

According to the invention, the lipase may typically be used as an additive in a detergent composition. This additive is conveniently formulated as a non-dusting granulate, a stabilized liquid, a slurry or a protected enzyme. Non-dusting granulates may be produced, e.g., as disclosed in U.S. Pat. Nos. 4,106,991 and 4,661,452 (both to Novo Industri A/S) and may optionally be coated by methods known in the art. Examples of waxy coating materials are poly(ethylene oxide) products (polyethylene glycol, PEG) with mean molecular weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in EP A suitable activity range for a detergent additive containing the lipolytic enzyme of this invention is 0.01–100 mg pure enzyme protein per g of the additive.

DETERGENT COMPOSITION

The detergent compositions of the invention may for example, be formulated as hand and machine laundry detergent compositions including laundry additive compositions and compositions suitable for use in the pretreatment of stained fabrics, rinse added fabric softener compositions, and compositions for use in general household hard surface cleaning operations and dishwashing operations.

The detergent composition of the invention comprises the lipase of the invention and a surfactant. Additionally, it may optionally comprise a builder, another enzyme, a suds suppresser, a softening agent, a dye-transfer inhibiting agent and other components conventionally used in detergents such as soil-suspending agents, soil-releasing agents, optical brighteners, abrasives, bactericides, tarnish inhibitors, coloring agents, and/or encapsulated or non-encapsulated perfumes.

The detergent composition according to the invention can be in liquid, paste, gels, bars or granular forms. The pH (measured in aqueous solution at use concentration) will usually be neutral or alkaline, e.g. in the range of 7–11, particularly 9–11. Granular compositions according to the present invention can also be in "compact form", i.e. they may have a relatively higher density than conventional granular detergents, i.e. form 550 to 950 g/l.

The lipase of the invention, or optionally another enzyme incorporated in the detergent composition, is normally incorporated in the detergent composition at a level from 0.00001% to 2% of enzyme protein by weight of the composition, preferably at a level from 0.0001% to 1% of enzyme protein by weight of the composition, more preferably at a level from 0.001% to 0.5% of enzyme protein by weight of the composition, even more preferably at a level from 0.01% to 0.2% of enzyme protein by weight of the composition.

The detergent composition of the invention may comprise the lipase in an amount corresponding to 10–50,000 LU per gram of detergent, preferably 20–5,000 LU/g, e.g. 100–1000 LU/g. The detergent may be dissolved in water to produce a wash liquor containing lipolytic enzyme in an amount corresponding to 25–15,000 LU per liter of wash liquor, particularly 100–5000 LU/l, e.g. 300–2000 LU/l. The amount of lipase protein may be 0.001–10 mg per gram of detergent or 0.001–100 mg per liter of wash liquor.

More specifically, the lipase of the invention may be incorporated in the detergent compositions described in WO 97/04079, WO 97/07202, WO 97/41212, PCT/DK WO 98/08939 and WO 97/43375.

Surfactant System

The surfactant system may comprise nonionic, anionic, cationic, ampholytic, and/or zwitterionic surfactants. As described above, the lipase variants of the invention are particularly suited for detergents comprising of a combination of anionic and nonionic surfactant with 70–100% by weight of anionic surfactant and 0–30% by weight of nonionic, particularly 80–100% of anionic surfactant and 0–20% nonionic. As further described, some preferred lipases of the invention are also suited for detergents comprising 40–70% anionic and 30–60% non-ionic surfactant.

The surfactant is typically present at a level from 0.1% to 60% by weight, e.g. 1% to 40%, particularly 10–40% preferably from about 3% to about 20% by weight. Some examples of surfactants are described below.

Anionic surfactants

Preferred anionic surfactants include alkyl sulfate, alkyl ethoxy sulfate, linear alkyl benzene sulfonate and mixtures of these.

The alkyl sulfate surfactants are water soluble salts or acids of the formula $ROSO_3M$ wherein R preferably is a $C_{10}$–$C_{24}$ hydrocarbyl, preferably an alkyl or hydroxyalkyl having a $C_{10}$–$C_{20}$ alkyl component, more preferably a $C_{12}$–$C_{18}$ alkyl or hydroxyalkyl, and M is H or a cation, e.g., an alkali metal cation (e.g. sodium, potassium, lithium), or ammonium or substituted ammonium.

Alkylbenzene sulfonates are suitable, especially linear (straight-chain) alkyl benzene sulfonates (LAS) wherein the alkyl group preferably contains from 10 to 18 carbon atoms.

Suitable anionic surfactants include alkyl alkoxylated sulfates which are water soluble salts or acids of the formula $RO(A)_mSO_3M$ wherein R is an unsubstituted $C_{10}$–$C_{24}$ alkyl or hydroxyalkyl group having a $C_{10}$–$C_{24}$ alkyl component, preferably a $C_{12}$–$C_{20}$ alkyl or hydroxyalkyl, more preferably $C_{12}$–$C_{18}$ alkyl or hydroxyalkyl, A is an ethoxy or propoxy unit, m is greater than zero, typically between about 0.5 and about 6, more preferably between about 0.5 and about 3, and M is H or a cation which can be, for example, a metal cation (e.g., sodium, potassium, lithium, calcium, magnesium, etc.), ammonium or substituted-ammonium cation. Alkyl ethoxylated sulfates as well as alkyl propoxylated sulfates are contemplated herein. Specific examples of substituted ammonium cations include methyl-, dimethyl, trimethyl-ammonium cations and quaternary ammonium cations such as tetramethyl-ammonium and dimethyl piperdinium cations and those derived from alkylamines such as ethylamine, diethylamine, triethylamine, mixtures thereof, and the like.

Other anionic surfactants include salts (including, for example, sodium, potassium, ammonium, and substituted ammonium salts such as mono- di- and triethanolamine salts) of soap, $C_8$–$C_{22}$ primary or secondary alkanesulfonates, $C_8$–$C_{24}$ olefinsulfonates, sulfonated polycarboxylic acids prepared by sulfonation of the pyrolyzed product of alkaline earth metal citrates.

Nonionic Surfactant

The surfactant may comprise polyalkylene oxide (e.g. polyethylene oxide) condensates of alkyl phenols. The alkyl group may contain from about 6 to about 14 carbon atoms, in a straight chain or branched-chain. The ethylene oxide may be present in an amount equal to from about 2 to about 25 moles per mole of alkyl phenol.

The surfactant may also comprise condensation products of primary and secondary aliphatic alcohols with about 1 to about 25 moles of ethylene oxide. The alkyl chain of the aliphatic alcohol can either be straight or branched, and generally contains from about 8 to about 22 carbon atoms.

Further, the nonionic surfactant may comprise polyethylene oxide condensates of alkyl phenols, condensation products of primary and secondary aliphatic alcohols with from about 1 to about 25 moles of ethylene oxide, alkylpolysaccharides, and mixtures hereof. Most preferred are $C_8$–$C_{14}$ alkyl phenol ethoxylates having from 3 to 15 ethoxy groups and $C_8$–$C_{18}$ alcohol ethoxylates (preferably $C_{10}$ avg.) having from 2 to 10 ethoxy groups, and mixtures thereof.

Preferred nonionic surfactants are alcohol ethoxylate, alcohol phenol ethoxylate, polyhydroxy fatty acid amide, alkyl polyglucoside and mixtures of these.

Builder System

The compositions according to the present invention may further comprise a builder system. Any conventional builder system is suitable for use herein including aluminosilicate materials, silicates, polycarboxylates and fatty acids, materials such as ethylenediamine tetraacetate (EDTA), metal ion sequestrants such as aminopolyphosphonates. Phosphate builders can also be used herein.

Suitable builders can be an inorganic ion exchange material, commonly an inorganic hydrated aluminosilicate material, more particularly a hydrated synthetic zeolite such as hydrated zeolite A, X, B, HS or MAP.

Detergency builder salts are normally included in amounts of from 5% to 80% by weight of the composition. Preferred levels of builder for liquid detergents are from 5% to 30%.

Other Enzymes

The detergent composition may, in addition to the lipase of the invention, comprise other enzyme(s) providing cleaning performance and/or fabric care benefits, e.g. proteases, lipases, cutinases, amylases, cellulases, peroxidases, oxidases (e.g. laccases).

Suitable proteases include those of animal, vegetable or microbial origin. Microbial origin is preferred. Chemically or genetically modified mutants are included. The protease may be a serine protease, preferably an alkaline microbial protease or a trypsin-like protease. Examples of alkaline proteases are subtilisins, especially those derived from Bacillus, e.g., subtilisin Novo, subtilisin Carlsberg, subtilisin 309, subtilisin 147 and subtilisin 168 (described in WO 89/06279) and variants thereof.

Bleaching Agents:

The detergent composition (especially in the case of a granular detergent) may also comprise a bleaching agents, e.g. an oxygen bleach or a halogen bleach. The oxyugen bleach may be a hydrogen peroxide releasing agent such as a perborate (e.g. PB1 or PB4) or a percarbonate, or it may e.g. be a percarboxylic acid. The particle size may be 400–800 microns. When present, oxygen bleching compounds will typically be present at levels of from about 1% to about 25%.

The hydrogen peroxide releasing agent can be used in combination with bleach activators such as tetraacetylethylenediamine (TAED), nonanoyloxybenzene-sulfonate (NOBS), 3,5-trimethyl-hexsanoloxybenzene-sulfonate (ISONOBS) or pentaacetylglucose (PAG).

The halogen bleach may be, e.g. a hypohalite bleaching agent, for example, trichloro isocyanuric acid and the sodium and potassium dichloroisocyanurates and N-chloro and N-bromo alkane sulphonamides. Such materials are normally added at 0.5–10% by weight of the finished product, preferably 1–5% by weight.

Model Detergents

Anionic Model Detergent A

A model granular detergent (90% anionic out of total surfactants, pH in solution 10.2) is made by mixing the following ingredients (% by weight):

8.7% anionic surfactant: LAS ($C_{10}$–$C_{13}$)

7.4% anionic surfactant: AS ($C_{12}$)

1.8% Nonionic surfactant: alcohol ethoxylate ($C_{12}$–$C_{15}$, 7EO)

30% Zeolite P (Wessalite P)

18% Sodium Carbonate

5% Sodium Citrate

17% Sodium sulfate 0.3% Carboxy-Methyl-Cellulose 6.5% Sodium-percarbonate monohydrate 2.1% NOBS Anionic model detergent B A second model granular detergent (79% anionic out of total surfactants, pH in solution 10.2) is made by mixing the following ingredients (% by weight):

27% anionic surfactant: AS ($C_{12}$)

7% Nonionic surfactant ($C_{12-15}$, 7EO)

60% Zeolite P (Wessalite P)

5% Sodium Carbonate 0.6% Sokalan CP5

1.5% Carboxy-Methyl-Cellulose

Anionic/non-ionic Model Detergent

A model detergent solution (32% anionic out of total surfactant, pH 10.2) is made by adding the following ingredients to 3.2 mM Ca2+/ Mg2+(5:1) in pure water:

0.300 g/l of alkyl sulphate (AS; C14–16);

0.650 g/l of alcohol ethoxylate (AEO; C12–14, 6EO);

1.750 g/l of Zeolite P 0.145 g/l of Na2CO3

0.020 g/l of Sokalan CP5

0.050 g/l of CMC (carboxy-methyl cellulose)

MATERIALS AND METHODS

Methods

Lipase Activity (LU)

A substrate for lipase is prepared by emulsifying glycerin tributyrate using gum Arabic as emulsifier. Lipase activity is assayed at pH 7 using pH stat method. One unit of lipase activity (LU) is defined as the amount needed to liberate one micromole fatty acid per minute.

Site-directed Mutagenesis

For the construction of variants of a Lipolase enzyme the commercial kit, Chameleon double-stranded, site-directed mutagenesis kit can be used according to the manufacturer's instructions.

The gene encoding the Lipolase enzyme in question is located on pAHL. In accordance with the manufacturer's instructions, the ScaI site of the Ampicillin gene of pAHL is changed to a MluI site by use of the primer 7258 (SEQ ID NO: 1), thus changing the ScaI site found in the ampicillin resistance gene and used for cutting to a MluI site.

The pAHL vector comprising the Lipolase gene in question is then used as a template for DNA polymerase and oligo 7258 and 7770 (SEQ ID NO: 2), thus changing the ScaI site found in the Lipolase gene and without changing the amino acid sequence site.

The desired mutation (e.g. the introduction of a cysteine residue) is introduced into the Lipolase gene in question by addition of an appropriate oligos comprising the desired mutation.

EXAMPLES

Example 1

Construction of Lipase Variant

Site directed mutagenesis as described above was used to construct a plasmid harboring a gene encoding the Lipolase variant 1S, E239C, Q249R. The following primers were used.

The primer 106659 (SEQ ID NO: 3) was used to introduce E99N,N101S.

The primer 101782 (SEQ ID NO: 4) was used to introduce SPPCGRRP (-E).

The primer 9639 (SEQ ID NO: 5) was used to introduce E239C.

The primer 8829 (SEQ ID NO: 6) was used to introduce Q249R.

Figure 1:
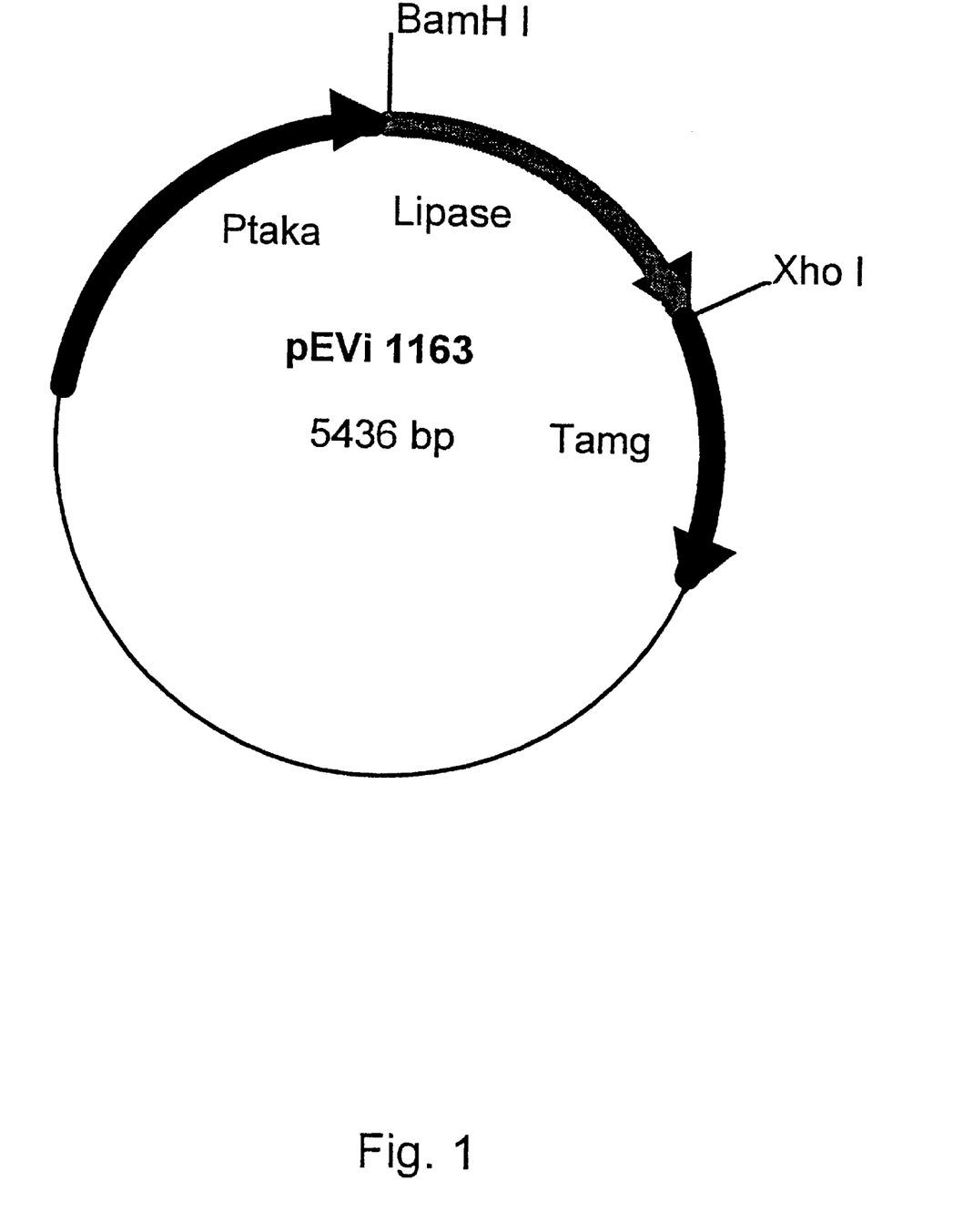
FIG. 1 shows the construction of plasmid pEVi 1163.

The mutations were verified by sequencing the whole gene. The resulting plasmid was called pEVi 1163, and a restriction map is shown is shown in FIG. 1.

Construction of the Aspergillus Vector pCaHj483

Figure 2:
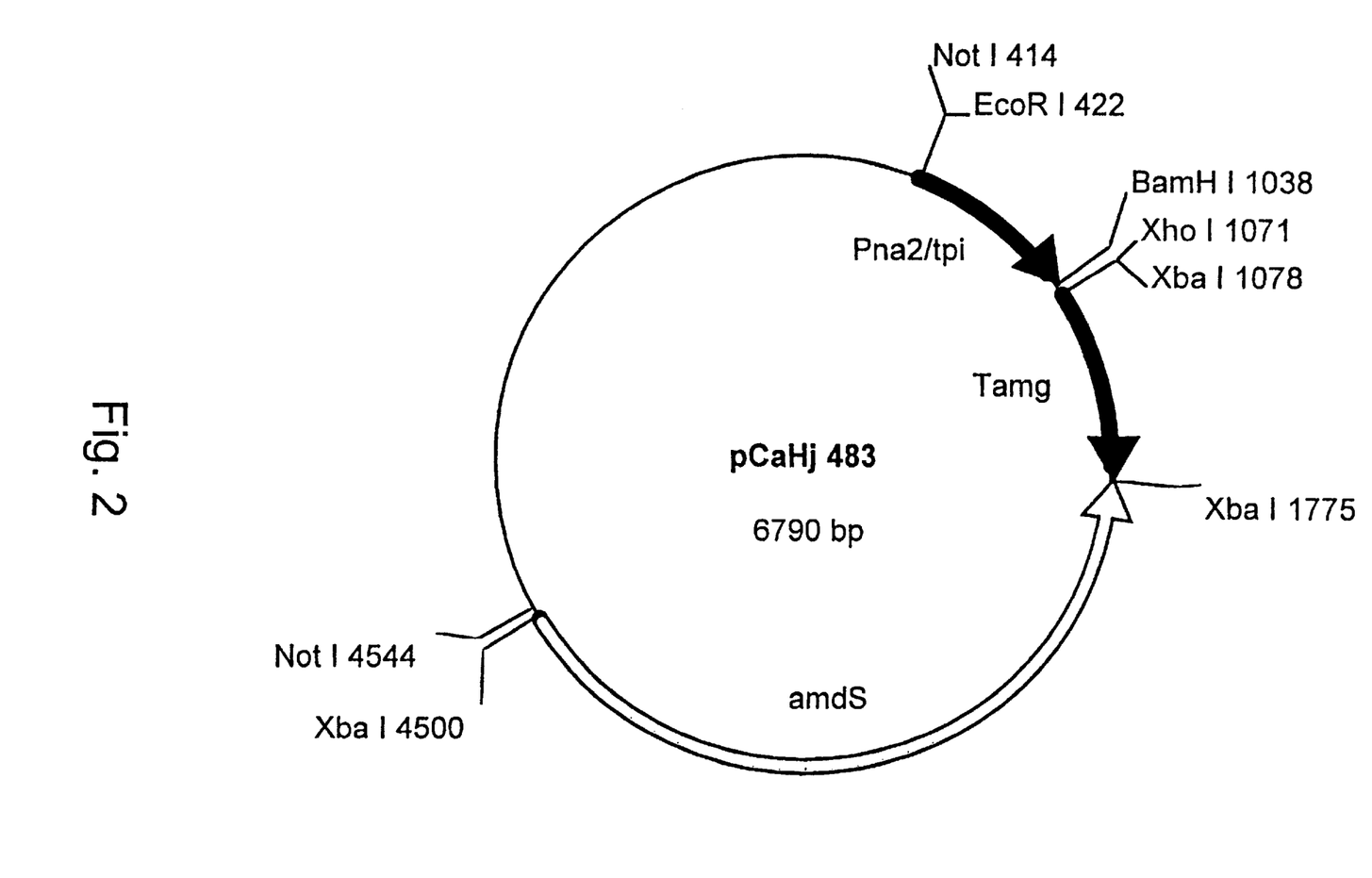
FIG. 2 shows the construction of the Aspergillus vector pCaHj 483.
Figure 3A:
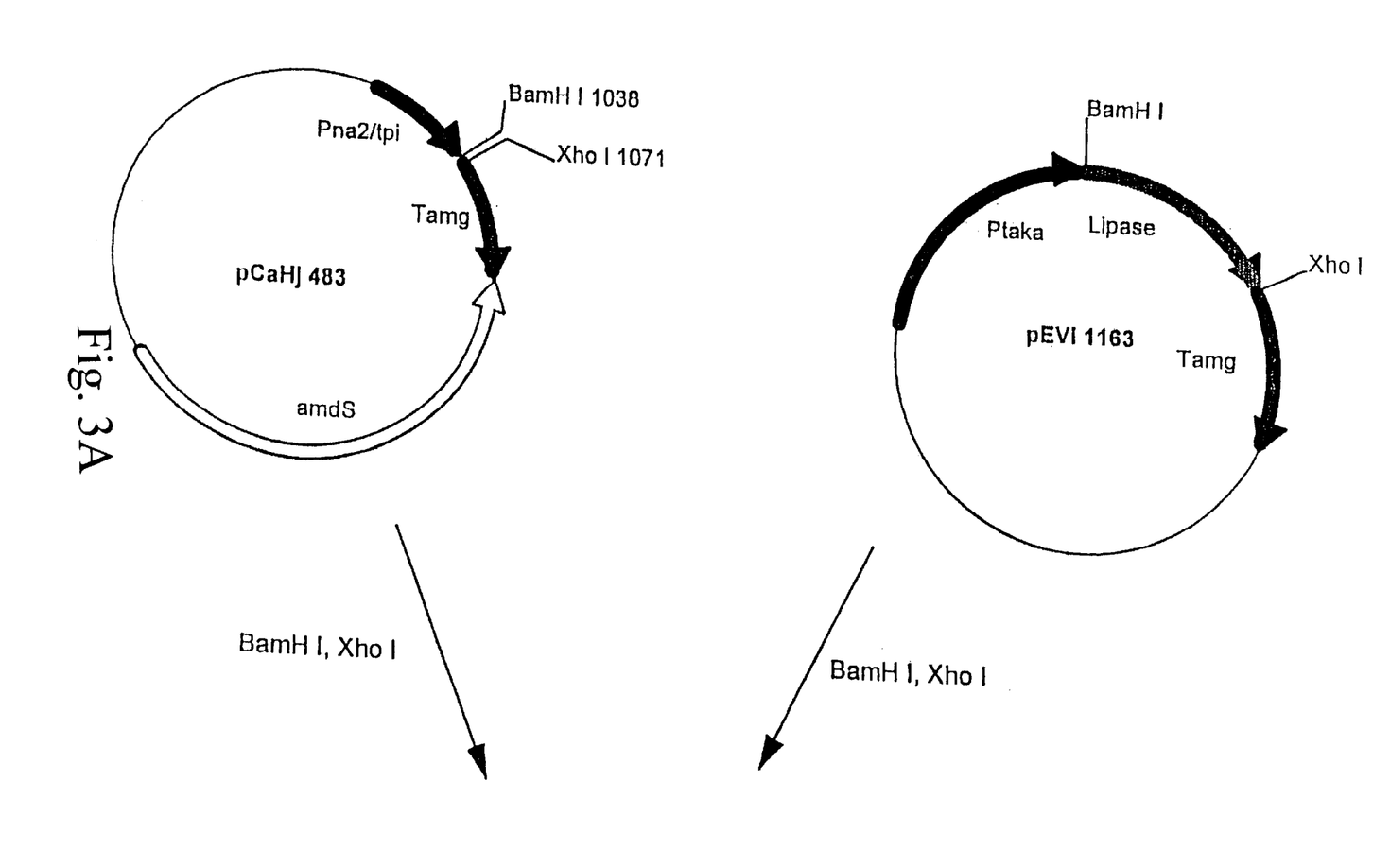
FIG. 3 shows the construction of the expression plasmid pCaHj 521.
Figure 3B:
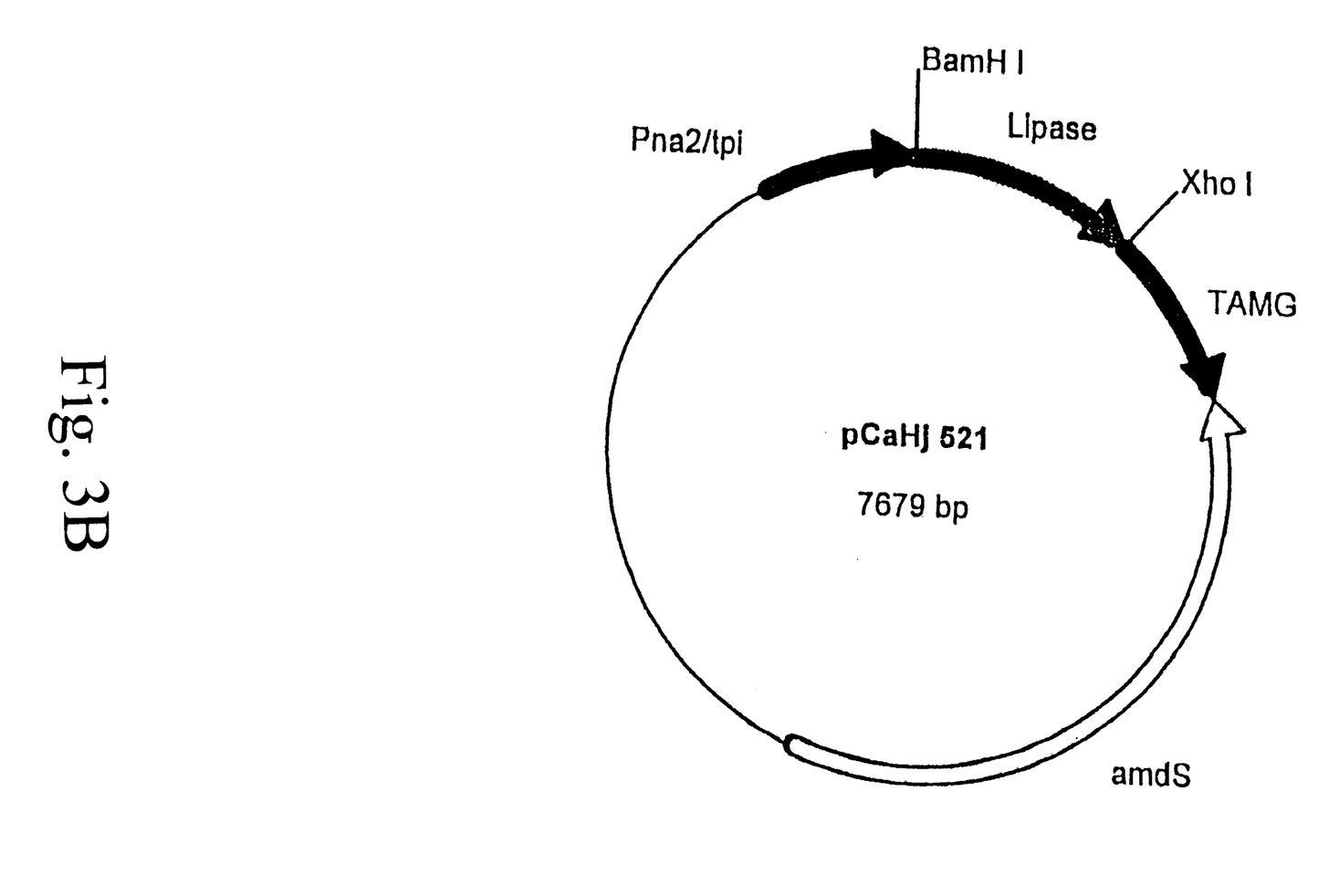

Aspergillus vector pCaHj483 shown in FIG. 2 was built from the following fragments:

a) The vector pToC65 (WO 91/17243) cut with EcoRI and XbaI.
b) A 2.7 kb XbaI fragment from *A. nidulans* carrying the amdS gene (C. M. Corrick et al. Gene 53 (1987), 63–71). The amdS gene is used as a selective marker in fungal transformations. The amdS gene has been modified so that the BamHI site normally present in the gene is destroyed. This has been done by introducing a silent point mutation using the primer shown in SEQ ID NO: 7.
c) A 0.6.kb EcoRIIBamHI fragment carrying the *A. niger* NA2 promoter fused to a 60bp DNA fragment of the sequence encoding the 5' untranslated end of the mRNA of the *A. nidulans* tpi gene. The NA2 promoter was isolated from the plasmid pNA2 (EP-B-O 383 779) fused to the 60 bp tpi sequence by PCR. The primer encoding the 60 bp tpi sequence had the sequence shown in SEQ ID NO: 8.
d) A 675 bp XbaI fragment carrying the *A. niger* glucoamylase transcription terminator. The fragment was isolated from the plasmid pICAMG/Term (EP 238023, application No. EP 87103806.3).

The BamHI site of fragment c was connected to the XbaI site in front of the transcription terminator on fragment d via the pIC19R linker (BamHI to XbaI)

Construction of the Expression Plasmid pCaHj 521.

The lipase variant plasmid pEVi 1163 was digested with BamHI and SalI, and the resulting fragment encoding the lipase variant was isolated.

pCaHj 483 was digested with BamHI and XhoI, and the large vector fragment (6757) was ligated to the lipase fragment. The ligation mixture was used to transform *E. coli* DH 5a cells, and a transformant harboring the expected plasmid was isolated. The plasmid was termed pCaHj 521.

Transformation of pCaHj 521 into JaL 228.

*Aspergillus oryzae* JaL 228 (PCT/DK 97/00037) is *Aspergillus oryzae* IFO 4177 deleted in the alkaline protease and the neutral metalloprotease 1. This strain was transformed with pCaHj 521 using selection on acetamide as described in patent EP 0 531 372 B1. Transformants were spore reisolated twice. Spores from second reisolation of each transformant were tested for lipase production in smaI scale fermentation (shake flasks and microtiterdishes).

Example 2

First-Wash Performance in Anionic Detergent

A number of variants according to the invention were tested in an anionic detergent. The experimental conditions were as follows:

| | |
|---|---|
| Equipment: | Thermostated Terg-o-tometer |
| Method: | 1 cycle wash followed by line drying. |
| Wash liquor: | 1000 ml per beaker |
| Swatches: | 7 (cotton style # 400) swatches (9*9 cm) per beaker. |
| Stain: | Lard coloured with Sudan red (0,75 mg Sudan red/g lard). |
| | 50 ml of lard/Sudan red heated to 70° C. is applied to the center of each swatch. After application of the stain the swatches are heated in an oven for 25 minutes at 75° C. Stored overnight at room temperature prior to the wash. |
| Water: | 1.07 mM $Ca^{2+}/Mg^{2+}$ (5:1) ~6°dH |
| Detergent: | 1.4 g/l commercial Tide w. Bleach. |
| Lipase concentration: | 0.1000 LU/I |
| Wash time: | 12 min. |
| Temperature: | 25° C. |
| Rinse: | 15 minutes in running tap water. |
| Drying: | Overnight at room temperature (~20° C., 30–40% RH). |

Evaluation: The reflectance was measured at 460 nm at a Machbeth Coloreye 7000 reflectometer. The results are given as ΔR (delta Reflectance)=reflectance of swatches washed in detergent with lipase minus reflectance of swatches washed in detergent without lipase

| Mutations | N-terminal | ΔR |
|---|---|---|
| N94K | SPPRRP(-E)(SEQ ID NO:11) | 3 |
| N94K + Q249R | SPPRRP(-E)(SEQ ID NO:11) | 4 |
| G91A + D96N + E99K + Q249R | SPIRPRP(-E)(SEQ ID NO:10) | 3 |
| G91A + D96E + E99K + Q249R | SPIRPRP(-E)(SEQ ID NO:10) | 3 |
| G91A + E99K + E239C + Q249R | SPPCGRRP(-E) (SEQ ID NO:12) | 3 |
| G91A + D96W + Q249R | SPIRPRP(-E)(SEQ ID NO:10) | 3 |
| G91A + E99K + Q249R | SPIRPRP(-E) (SEQ ID NO:10) | 4 |
| E239C | SPPCGRRP(-E) (SEQ ID NO:12) | 3 |
| S83T + N94K + D96L + E239C + Q249R | (SPCRPRP(-E) (SEQ ID NO:14) | 3 |
| E99N + N101S + E239C + Q249R | SPPCGRRP(-E) (SEQ ID NO:12) | 4 |
| E99K + Q249R | SPIRPRP(-E) (SEQ ID NO:10) | 2 |
| G91A + Q249R | SPIRPRP(-E) (SEQ ID NO:10) | 4 |
| G91A + E99K | SPIRPRP(-E) (SEQ ID NO:10) | 4 |
| E99N + N101S + E239C | SPPCGRRP(-E) (SEQ ID NO:12) | 4 |
| G91A + E99N + N101S + E239C + Q249R | SPPCGRRP(-E) (SEQ ID NO:12) | 3 |
| S83T + E99N + N101S + E239C + Q249R | SPPCGRRP(-E) (SEQ ID NO:12) | 5 |
| E99N + E239C + Q249R | SPPCGRRP(-E) (SEQ ID NO:12) | 3 |
| N101S + E239C + Q249R | SPPCGRRP(-E) (SEQ ID NO:12) | 2 |
| D96S + E239C + Q249R | SPPCGRRP(-E) (SEQ ID NO:12) | 3 |
| N94S + D96L + E239C + Q249R | SPPCGRRP(-E) (SEQ ID NO:12) | 3 |
| E99K + E239C + Q249R | SPPCGRRP(-E) (SEQ ID NO:12) | 3 |
| Q249R | SPIRPRP(-E) (SEQ ID NO:10) | 3 |
| K98D + E99K + Q249R | SPIRPRP(-E) (SEQ ID NO:10) | 3 |
| E99K + D137E + Q249R | SPIRPRP(-E) (SEQ ID NO:10) | 4*) |
| E99K,R209P,Q249R | SPIRPRP(-E) (SEQ ID NO:10) | 2 |
| E99K,R209S,Q249R | SPIRPRP(-E) (SEQ ID NO:10) | 3***) |
| E99K,D137E,E183D,E239C,Q249R | SPPCGRRP(-E) (SEQ ID NO:12) | 2 |
| E99K,R209P,E239C,Q249R | SPPCGRRP(-E) (SEQ ID NO:12) | 6 |
| N94D,E99N,E239C,Q249R | SPPCGRRP(-E) (SEQ ID NO:12) | 5 |
| S83T + Q249R | SPIRR(SEQ ID NO:9) | 5 |
| S83T + E87K + Q249R | SPIRR(SEQ ID NO:9) | 3*)**) |
| D57G + W89F + I90V + G91S + Q249R | SPIRPRP(-E) (SEQ ID NO:10) | 4 |
| E1A + N11H + L12I + D137G + V187A + K237R + T244S + Q249R | SPIRR(SEQ ID NO:9) | 2 |
| N8K + F10L + N11C + Q15H + R232G + E239C | SPPCGRRP(-E) (SEQ ID NO:12) | 3 |
| T231K + R232G + N233H + E239C | SPPCGRRP(-E) (SEQ ID NO:12) | 3 |

\* Special wash conditions: 1250 LU/I
\*\* Special wash conditions: 30° C., 20 min wash
\*\*\* Special wash conditions: 500 LU/I For comparison, the following lipase variant according to WO 97/07202 was tested at the same conditions:

Prior art: Lipolase modified with E1SPIRPRP (SEQ ID NO: 10)+D57G+N94K+D96L+L97M+Q249R.

The result showed ΔR=1.3 at 1000 LU/I of the prior-art lipase variant. Thus, the results show clearly that the lipase variants have improved first-wash effect in a detergent with mainly anionic surfactant (more than 80% of total surfactant).

Example 3

Comparative Test for First-wash Effect

A lipase variant of the invention was compared to a prior-art lipase variant according to WO97/07202, as follows:

Invention: Lipolase modified with E1SPPCGRRP (SEQ ID NO: 12)+E99N+N101S+E239C+Q249R. Prior art: Lipolase modified with E1SPPRRP (SEQ ID NO: 11)+D57G+N94K+D96L+Q249R.

|  | 1250 LU/I | 12,500 LU/I |
|---|---|---|
| Invention | 4.9 | 11.1 |
| Prior art | 2.1 | 8.3 |

The results show in each case that the variant of the invention has a better first-wash effect in anionic detergent than the prior-art variant.

Example 4

First-Wash Performance in Various Detergents

The lipase variant was Lipolase with modifications E1SPPCGRRP (SEQ ID NO: 12)+E99N+N101S+E239C+Q249R, prepared in Example 1. The following two detergents were tested at the same conditions as in Example 2:

Anionic detergent

Water: 1.07 mM Ca2+/Mg2+ (5:1) ~6°dH
Detergent: 1.4 g/l commercial Tide w. Bleach.
Lipase concentration: 0, 800, 1600, 3200, 6400, 12800 LU/I
Wash time: 12 min.
Temperature: 30° C.

Anionic/non-ionic detergent

Water: 3.2 mM Ca2+/Mg2+ (5:1) ~18°dH
Detergent: 3.6 g/l commercial Ariel Futur.
Lipase concentration: 0, 800, 1600, 3200, 6400, 12800 LU/I
Wash time: 20 min.
Temperature: 30° C.

| Variant dosage | Anionic detergent | Anionic/non-ionic detergent |
|---|---|---|
| 800 LU/I | 4 | 6 |
| 1600 LU/I | 7 | 7 |
| 3200 LU/I | 7 | 8 |
| 6400 LU/I | 10 | 10 |
| 12800 LU/I | 11 | 11 |

The above results show that the lipase variant has a good first-wash performance, both in a detergent with more than 80% anionic surfactant and in a detergent with about equal amounts of anionic and non-ionic surfactant.

Example 5

Stability in Detergent Solutions

To evaluate stability of the lipase variant in detergent solutions, residual activity after incubation was determined.

Two detergents with high content (>80%) of anionic surfactant were tested: a commercial U.S. detergent (Tide w. Bleach HDP at 1.4 g/l) and a Japanese detergent (Super Compact Top at 0.5 g/l). A detergent with nearly equal amounts of anionic and non-ionic surfactants was also tested: a commercial European detergent (Ariel Futur HDP at 5 g/l).

A solution of each detergent was heated to 85° C. for 5 minutes to inactivate the enzymes. The detergent solution was cooled to room temperature and the pH was adjusted to pH 10.0. Purified lipase was added to a concentration of approx. 10 LU/ml in a 5 ml volume and the solution was split into two portions:

a) One for immediate determination of activity (reference), and b) One for 30 minutes incubation at 30° C. (sample).

100 μl samples were taken from solutions a) and b) (upon rapid cooling) for determination in duplicate of the activity by the LU method described above.

The residual activity after incubation was calculated as the activity in sample

| Surfactant | Detergent | Residual activity |
|---|---|---|
| Mainly anionic | US | 65% |
| Mainly anionic | Japanese | >90% |
| Anionic + non-ionic | European | 91% | b) relative to the activity in sample a). The results were as follows:

A similar experiment with the European detergent solution at 40° C. showed 61% residual activity after 20 minutes.

The results show that the lipase variant is fairly stable in detergent solutions, both with mainly anionic surfactant and with nearly equal amounts of anionic and non-ionic surfactants.

What is claimed is:

1. An isolated lipase which is a polypeptide having an amino acid sequence which:
   has at least 90% identity with the wild-type lipase derived from *Humicola lanuginosa* strain DSM 4109 (SEQ ID NO: 19);
   compared to said wild-type lipase, comprises a positively charged peptide extension attached to the N-terminal;
   comprises a negative amino acid in position E210 of said wild-type lipase;
   comprises a negatively charged amino acid in the region corresponding to positions 90–101 of said wild-type lipase; and
   comprises a neutral or negative amino acid at a position corresponding to N94 of said wild-type lipase and/or has a negative or neutral net electric charge in the region corresponding to positions 90–101 of said wild-type lipase.

2. An isolated lipase which is a polypeptide having an amino acid sequence which:
   has at least 90% identity with the wild-type lipase derived from *Humicola lanuginosa* strain DSM 4109 (SEQ ID NO: 19);
   compared to said wild-type lipase, comprises a positively charged peptide extension attached to the N-terminal;
   comprises a negative amino acid in position E210 of said wild-type lipase; and
   comprises amino acids with negative or unchanged electric charge in at least two of positions N94, D96 and E99 of said wild-type lipase.

3. The lipase of claim 1 wherein the peptide extension consists of 1–15 amino acid residues.

4. The lipase of claim 3 wherein the extension is SPIRR (SEQ ID NO: 9), RP(-E), SPIRPRP(-E) (SEQ ID NO: 10), SPPRRP(-E) (SEQ ID NO: 11) or SPIRPRP(-E) (SEQ ID NO: 10).

5. The lipase of claim 1 wherein the extension comprises a first cysteine which is attached to a second cysteine in the polypeptide.

6. The lipase of claim 1 which comprises a substitution G91A, N94D/E/K/R, D96E/I/L/N/S/W, E99N/Q/K/R/H, N101S, R209P/S or Q249R/K/H.

7. The lipase of claim 1 which comprises one of the following sets of substitutions:
   G91G/A/S/T+N94(neutral or negative)+D96D/E/C/Y+E99E/D/C/Y,
   G91G/A/S/T+N94(neutral or negative)+D96D/E/C/Y+E99N+N101S,
   G91G/A/S/T+N94R/K/H+D96D/E/C/Y+E99E/D/C/Y,
   G91G/A/S/T+N94(neutral or negative)+D96(neutral or positive)+E99E/D/C/Y, or
   G91G/A/S/T+N94(neutral or negative)+D96D/E/C/Y+E99(neutral or positive).

8. The lipase of claim 1 which comprises one of the following sets of substitutions:
   E99R/K/H+Q249R/K/H,
   N94R/K/H+Q249R/K/H, or
   D96(neutral or positive)+Q249R/K/H.

9. A lipase which is a variant of a parent lipase derived from *Humicola lanuginosa* strain DSM 4109 (SEQ ID NO: 19) having the modifications:
   a) E99N+N101S+E239C+Q249R+SPPCGRRP(-E) (SEQ ID NO: 12),
   b) E99K+E239C+Q249R+SPPCGRRP(-E)(SEQ ID NO: 12), or
   c) E99N+E239C+Q249R+SPPCGRRP(-E)(SEQ ID NO: 12).

10. A detergent composition comprising a surfactant and the lipase of claim 1.

11. The detergent composition of claim 10 wherein the surfactant comprises anionic surfactant in an amount of more than 70% by weight of the total surfactant.

12. The detergent composition of claim 10, wherein the surfactant comprises anionic surfactant in an amount of 40–70% by weight and nonionic surfactant in an amount of 30–60% by weight of the total surfactant.

13. The detergent composition of claim 10 which comprises 10–40% by weight of a surfactant.

14. The lipase of claim 1 wherein the peptide extension consists of 4–10 amino acid residues.

15. The lipase of claim 1 wherein the peptide extension comprises a positively charged amino acid.

16. The lipase of claim 1 wherein the peptide extension comprises 1 to 3 positively charged amino acids.

17. The lipase of claim 1 wherein the peptide extension comprises an arginine.

18. The lipase of claim 1 wherein the peptide extension comprises 1–3 arginine amino acid residues.

19. The lipase of claim 5, wherein the second cysteine is an a peptide extension selected from the group consisting of SPPCGRRP(-E)(SEQ ID NO: 12), SPCRPR(SEQ ID NO: 13), SPCRPRP(-E) (SEQ ID NO: 14), SPPCGRRPRRP(-E) (SEQ ID NO: 15), SPPNGSCGRRP(-E) (SEQ ID NO: 16), SPPCRRRP(-E) (SEQ ID NO: 17) and SCIRR(SEQ ID NO: 18).

20. The lipase of claim 19, wherein the first cysteine is introduced by the substitution E239C.

21. The lipase of claim 7 which further comprises Q249R/K/H and/or K98X.

22. The lipase of claim 8 which further comprises Q249R and/or R209(neutral or negative).

23. The detergent composition of claim 13 which comprises 40–70% of a builder.

24. The detergent composition of claim 23, which has a pH of 9–11 when dissolved in water at 0.5–5 g/l.

* * * * *

SEQUENCE LISTING

<160> NUMBER OF SEQ ID NOS: 19

<210> SEQ ID NO 1
<211> LENGTH: 31
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(1)
<223> OTHER INFORMATION: n in position 1 denotes a,g,c, or t

<400> SEQUENCE: 1
ngaatgactt ggttgacgcg tcaccagtca c                31

<210> SEQ ID NO 2
<211> LENGTH: 27
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(1)
<223> OTHER INFORMATION: n in position 1 denotes a,g,c, or t

<400> SEQUENCE: 2
ntctagccca gaatactgga tcaaatc                27

<210> SEQ ID NO 3
<211> LENGTH: 40
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(1)
<223> OTHER INFORMATION: n in position 1 denotes a, g, c, or t

<400> SEQUENCE: 3
ncttaacttt gacttgaaaa acatatctga catttgctcc                40

```
<210> SEQ ID NO 4
<211> LENGTH: 60
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(1)
<223> OTHER INFORMATION: n in position 1 denotes a, g, c, or t

<400> SEQUENCE: 4
nggacggcct tggctagccc tccgtgcggc cgccggccgg tctcgcagga tctgtttaac    60

<210> SEQ ID NO 5
<211> LENGTH: 33
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(1)
<223> OTHER INFORMATION: n in position 1 denotes a, g, c, or t

<400> SEQUENCE: 5
natatcgtga agatatgcgg cattgatgcc acc    33

<210> SEQ ID NO 6
<211> LENGTH: 36
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(1)
<223> OTHER INFORMATION: n in position 1 denotes a, g, c, or t

<400> SEQUENCE: 6
nggcggcaat aaccggccga acattccgga tatccc    36

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
agaaatcggg tatcctttca g    21

<210> SEQ ID NO 8
<211> LENGTH: 105
<212> TYPE: DNA
<213> ORGANISM: Artificial Sequence
<220> FEATURE:
<223> OTHER INFORMATION: Primer

<400> SEQUENCE: 8
gctcctcatg gtggatcccc agttgtgtat atagaggatt gaggaaggaa gagaagtgtg    60
gatagaggta aattgagttg gaaactccaa gcatggcatc cttgc    105

<210> SEQ ID NO 9
<211> LENGTH: 5
<212> TYPE: PRT
<213> ORGANISM: Artificial Sequence
<220> FEATURE:
```

```
<223> OTHER INFORMATION: Synthetic

<400> SEQUENCE: 9

Ser Pro Ile Arg Arg
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic

<400> SEQUENCE: 10

Ser Pro Ile Arg Pro Arg Pro
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic

<400> SEQUENCE: 11

Ser Pro Pro Arg Arg Pro
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic

<400> SEQUENCE: 12

Ser Pro Pro Cys Gly Arg Arg Pro
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic

<400> SEQUENCE: 13

Ser Pro Cys Arg Pro Arg
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic

<400> SEQUENCE: 14

Ser Pro Cys Arg Pro Arg Pro
1               5

<210> SEQ ID NO 15
<211> LENGTH: 11
<212> TYPE: PRT
<213> ORGANISM: Artificial Sequence
<220> FEATURE:
<223> OTHER INFORMATION: Synthetic
```

```
<400> SEQUENCE: 15

Ser Pro Pro Cys Gly Arg Arg Pro Arg Pro
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Synthetic

<400> SEQUENCE: 16

Ser Pro Pro Asn Gly Ser Cys Gly Arg Arg Pro
1               5                   10

<210> SEQ ID NO 17
<211> LENGTH: 8
<212> TYPE: PRT
<213> ORGANISM: Artificial Sequence
<220> FEATURE:
<223> OTHER INFORMATION: Synthetic

<400> SEQUENCE: 17

Ser Pro Pro Cys Arg Arg Arg Pro
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic

<400> SEQUENCE: 18

Ser Cys Ile Arg Arg
1               5

<210> SEQ ID NO 19
<211> LENGTH: 269
<212> TYPE: PRT
<213> ORGANISM: Humicola lanuginosa
<220> FEATURE:
<221> NAME/KEY: mat_peptide
<222> LOCATION: (1)..()

<400> SEQUENCE: 19

Glu Val Ser Gln Asp Leu Phe Asn Gln Phe Asn Leu Phe Ala Gln Tyr
1               5                   10                  15

Ser Ala Ala Ala Tyr Cys Gly Lys Asn Asn Asp Ala Pro Ala Gly Thr
                20                  25                  30

Asn Ile Thr Cys Thr Gly Asn Ala Cys Pro Glu Val Glu Lys Ala Asp
            35                  40                  45

Ala Thr Phe Leu Tyr Ser Phe Glu Asp Ser Gly Val Gly Asp Val Thr
        50                  55                  60

Gly Phe Leu Ala Leu Asp Asn Thr Asn Lys Leu Ile Val Leu Ser Phe
65                  70                  75                  80

Arg Gly Ser Arg Ser Ile Glu Asn Trp Ile Gly Asn Leu Asn Phe Asp
                85                  90                  95

Leu Lys Glu Ile Asn Asp Ile Cys Ser Gly Cys Arg Gly His Asp Gly
            100                 105                 110

Phe Thr Ser Ser Trp Arg Ser Val Ala Asp Thr Leu Arg Gln Lys Val
        115                 120                 125
```

-continued

```
Glu Asp Ala Val Arg Glu His Pro Asp Tyr Arg Val Val Phe Thr Gly
    130                 135                 140

His Ser Leu Gly Gly Ala Leu Ala Thr Val Ala Gly Ala Asp Leu Arg
145                 150                 155                 160

Gly Asn Gly Tyr Asp Ile Asp Val Phe Ser Tyr Gly Ala Pro Arg Val
                165             170                 175

Gly Asn Arg Ala Phe Ala Glu Phe Leu Thr Val Gln Thr Gly Gly Thr
                180             185                 190

Leu Tyr Arg Ile Thr His Thr Asn Asp Ile Val Pro Arg Leu Pro Pro
        195                 200                 205

Arg Glu Phe Gly Tyr Ser His Ser Ser Pro Glu Tyr Trp Ile Lys Ser
    210                 215                 220

Gly Thr Leu Val Pro Val Thr Arg Asn Asp Ile Val Lys Ile Glu Gly
225                 230                 235                 240

Ile Asp Ala Thr Gly Gly Asn Asn Gln Pro Asn Ile Pro Asp Ile Pro
                245                 250                 255

Ala His Leu Trp Tyr Phe Gly Leu Ile Gly Thr Cys Leu
                260             265
```